United States Patent [19]

Weil

[11] Patent Number: 5,418,355
[45] Date of Patent: * May 23, 1995

[54] STORAGE PHOSPHOR RADIOGRAPHY PATIENT IDENTIFICATION SYSTEM

[75] Inventor: Richard Weil, Pittsford, N.Y.

[73] Assignee: Eastman Kodak Company, Rochester, N.Y.

[*] Notice: The portion of the term of this patent subsequent to Nov. 23, 2010 has been disclaimed.

[21] Appl. No.: 106,101

[22] Filed: Aug. 12, 1993

Related U.S. Application Data

[62] Division of Ser. No. 981,701, Nov. 25, 1992, Pat. No. 5,264,684.

[51] Int. Cl.⁶ .......................... G06K 7/10; G06K 7/00
[52] U.S. Cl. .................................. 235/375; 250/580; 250/584
[58] Field of Search ............... 250/584, 580, 581, 582; 235/375

[56] References Cited

U.S. PATENT DOCUMENTS

| | | |
|---|---|---|
| Re. 31,847 | 3/1985 | Luckey . |
| 4,641,242 | 2/1987 | Kimura . |
| 4,739,480 | 4/1988 | Oono et al. ............. 250/584 |
| 4,835,372 | 5/1989 | Gombrich et al. . |
| 4,857,713 | 8/1989 | Brown . |
| 4,857,716 | 8/1989 | Gombrich et al. . |
| 4,885,468 | 12/1989 | Shimura . |
| 4,960,994 | 10/1990 | Müller et al. ............. 250/584 |
| 5,006,699 | 4/1991 | Felkner et al. . |
| 5,065,866 | 11/1991 | Boutet et al. ............. 250/581 |
| 5,151,592 | 9/1992 | Boutet et al. . |
| 5,237,601 | 8/1993 | Boutet et al. ............. 378/182 |
| 5,264,684 | 11/1993 | Weil ............................ 235/375 |
| 5,311,032 | 5/1994 | Montoro et al. ............. 250/581 |
| 5,334,851 | 8/1994 | Good et al. ............. 250/582 |

Primary Examiner—Davis L. Willis
Assistant Examiner—Peter J. Rashid
Attorney, Agent, or Firm—William F. Noval

[57] ABSTRACT

A storage phosphor radiography patient identification system which matches a patient with an x-ray image of the patient stored in a storage phosphor. The system includes a patient identifying bar code—uniquely identifying a patient; a storage phosphor identifying bar code uniquely identifying a storage phosphor and a portable bar code scanner. The bar code scanner is used to scan the patient bar code and the storage phosphor bar code when a patient is exposed to an X-ray which is stored on the storage phosphor. Preferably, a portable x-ray source has a chart having sets of bar codes identifying x-ray examination type information. The bar code scanner scans the examination type bar codes at the time the x-ray of the patient is taken. The storage phosphor has a non-volatile read/write memory adhered to it. The bar code scanner has a memory probe which transfers the patient ID, storage phosphor ID and exam time information from the bar code scanner to the storage phosphor memory. The system includes a storage phosphor reader for converting an x-ray image stored in a storage phosphor into an x-ray image signal and for reading the bar code identification of the storage phosphor. The storage phosphor reader receives from the storage phosphor memory through an internal memory probe, information relating to patient identification, storage phosphor identification and examination type and matches the patient identification and examination type with the x-ray image signal.

5 Claims, 5 Drawing Sheets

| 70A PROJECTION | 70B BODYPART | 70C POSITION | 70D DISTANCE | 70E KVP | 70F MAS | 70G ORIENTATION | 70H COMMENTS |
|---|---|---|---|---|---|---|---|
| AP | CHEST | SUPINE | 40 | 50 | 1.25 | | NONE |
| LATERAL | SKULL | SEMI-ERECT | 42 | 60 | 1.5 | | |
| RLD | ABDOMEN | ERECT | 45 | 70 | 2.5 | | |
| LLD | CSPINE | | 50 | 80 | 3.2 | | |
| X TABLE | PELVIS | | 72 | 85 | 50 | | |
| | EXTREMITY | | | | 80 | | |

STORAGE PHOSPHOR RADIOGRAPHY PATIENT IDENTIFICATION SYSTEM

CROSS-REFERENCE TO RELATED APPLICATIONS

This application is a divisional application of U.S. patent application Ser. No. 07/981,701, filed Nov. 25, 1992, now U.S. Pat. No. 5,264,684.

FIELD OF THE INVENTION

This invention relates in general to storage phosphor radiography in which a latent x-ray image of a patient stored in a storage phosphor is converted to an x-ray image signal. More particularly, the present invention relates to a storage phosphor radiography patient identification system for matching patient x-ray exam data with the patient's x-ray image.

BACKGROUND ART

In conventional film/screen radiography, a commonly used patient identification system has the following features.

1. A requisition is filled out by the radiologist ordering a specific exam to be performed on a patient. The requisition is sent to the radiology department.
2. A technologist takes the requisition, an x-ray film cassette, and a portable x-ray generator to the patient bedside.
3. The technologist performs the exam and the film is exposed to x-rays.
4. The requisition is taped to the cassette and the exposed film is taken to the darkroom.
5. A preprinted information card is "flashed" on to the film. Such information includes the patient name, medical record number, birth date, hospital name, current date and other standard information.
6. The film is processed, and the radiology technologist verifies that a "good" image has been recorded.
7. A sticker is applied to the film which records the date, time of exposure, technique, and technologist identification.
8. The finished x-ray film is placed on a light box for review and diagnosis by a radiologist or physician.

Because of the inherent disadvantages of film radiography in the acquisition, storage and transmission of x-ray images, there has been proposed a storage phosphor radiography system. Temporary x-ray images stored in a storage phosphor are converted into an x-ray image digital signal which can be stored, processed and transmitted. As described in U.S. Pat. No. Re. 31,847, reissued Mar. 12, 1985 to Luckey, a photostimulable phosphor sheet is exposed to an image-wise pattern of short wavelength radiation, such as x-ray radiation, to record a latent image pattern in the photostimulable phosphor sheet. The latent image is read out by stimulating the phosphor with a relatively long wavelength stimulating radiation, such as red or infrared light. Upon stimulation, the stimulable phosphor releases emitted radiation of an intermediate wavelength, such as blue or violet light, in proportion to the quantity of x-ray radiation that was received. An x-ray image signal is produced by scanning the stimulable phosphor sheet in a raster pattern by means of a beam of laser light deflected by an oscillating or rotating scanning mirror. The emitted radiation is sensed by a photodetector to produce an electrical x-ray image signal. This signal may then be stored, transmitted, or displayed on a monitor or reproduced as an x-ray film.

As with film-based radiography, storage phosphor radiography requires the matching of an x-ray image with the patient. In situations where many x-rays are taken, such as in an intensive care unit of a large hospital, the management of identification of x-rays with patients can be monumental. In order to process an x-ray image signal as a function of x-ray exposure conditions, it is also desirable to match x-ray exposure conditions and other patient identification data with the x-ray image signal. Such matching results in proper diagnosis by a diagnostician (such as a radiologist) who views the x-ray image on a monitor or x-ray film reproduction.

In a known storage phosphor radiography system, patient information is entered into a workstation and is transferred to a magnetic card. (See, for example, U.S. Pat. Nos. 4,641,242, issued Feb. 3, 1987, inventor Kimura; 4,739,480, issued Apr. 19, 1988, inventors Oona et al.; 4,885,468, issued Dec. 5, 1989, inventor Shimura.) After an x-ray exposure on a storage phosphor is made, a technician places the cassette containing the exposed storage phosphor into a reader and dumps the patient data into the reader by swiping the magnetic card through an associated magnetic card reader. Many problems exist with this system, including double entry of patient data, which is typically entered into a computer at the time a patient is admitted into a hospital. Moreover, the specific ordering of computed radiography cassettes and patient data must be maintained.

U.S. Pat. No. 4,960,994, issued Oct. 2, 1990, inventor Muller et al., discloses a cassette which contains an x-ray film coated with a stimulable phosphor layer and which has a cassette memory which is rigidly attached to the cassette. The memory carries storable, recordable, readable, and erasable data and is attached to the cassette at a position spaced a predetermined distance from a given cassette corner. The rigidly attached memory has four contacts for transfer of data and for power supply. This patent does not disclose the use of a separate bar code on the cassette.

The health care bar code identification systems disclosed in the following patents are not entirely suitable for use in storage phosphor radiography systems: U.S. Pat. Nos. 4,857,713, issued Aug. 15, 1989, inventor Brown; 5,006,699, issued Apr. 9, 1991, inventors Felkner et al.; 4,835,372, issued May 30, 1989, inventors Gombrich et al.; and 4,857,372, issued Aug. 15, 1989, inventors Gombrich et al.

A storage phosphor radiography patient ID system using a hand-held bar code scanner has been proposed in commonly-assigned, copending U.S. patent application Ser. No. 963,036, filed Oct. 19, 1992. The disclosed system records data using a hand-held bar code scanner. Because this image will be recorded, processed, transmitted, and archived digitally by a computer, the exam data also needs to be in digital form to travel with the image. The exam data is read in directly from the bar code scanner by the storage phosphor reader into a header file which is associated with the image file. The image is quality assured by a radiology tech using an electronic view box(video monitor), and the image is printed on film with the necessary information by a laser printer. Thus, no "post-processing" is required.

A more recent development for use in healthcare identification systems is suggested in the brochure entitled "Touch The Future", distributed by Dallas Semiconductor, Dallas, Tex. A solid state read/write memory in a self contained stainless steel can has a self-adhesive backing attachable to a hospital bracelet to provide patient ID. A hospital bedside testing application is also suggested in which the solid state memory container is adhered to a nurse's badge and a reagent cannister. A hand-held meter downloads the information received from these memories into a personal computer. There is no suggestion in this brochure of using the solid state memory container in a storage phosphor radiography system.

A problem therefore exists in storage phosphor radiography apparatus of linking examination information associated with an x-ray exam with the x-ray image recorded in a storage phosphor.

SUMMARY OF THE INVENTION

According to the present invention, there is provided a storage phosphor radiography identification system which provides a solution to the problems of known film-based radiography and computed radiography identification systems. According to the present invention, a storage phosphor radiography patient identification system comprises:

patient identifying bar code means adapted to be located with a patient for identifying a patient;

a storage phosphor cassette means for containing a storage phosphor which stores an x-ray image of a patient, said storage phosphor cassette means having storage phosphor identifying bar code means for identifying said storage phosphor and further having adhered to it a read/write non-volatile memory contained in a self adhesive electrically conductive cylindrical container;

x-ray examination type bar code means locatable with an x-ray source for identifying x-ray examination type characteristics of an x-ray image stored in said storage phosphor, wherein said x-ray examination type bar code means includes a first set of bar codes identifying unique body parts of a patient and a second set of bar codes identifying x-ray exposure conditions;

hand-held bar code scanner means, having memory, for scanning said patient identifying bar code means, said storage phosphor bar code identifying means, and a bar code from each of said respective sets of said x-ray examination type bar code means at the time said storage phosphor means is exposed to an x-ray image of a patient, to produce patient identifying information, storage phosphor means identifying information, and x-ray examination type information which is stored in said memory; wherein said bar code scanner means is further provided with a probe connected to said memory for transferring said identifying information to said read/write non-volatile memory, adhered to said storage phosphor means;

storage phosphor reader means for converting a stored x-ray image in said storage phosphor into an x-ray image signal, said storage phosphor reader means having, a) bar code reader means for reading said storage phosphor bar code identifying means to produce a storage phosphor identifying signal matched with said x-ray image signal, and b) a read/write memory probe for contacting said read/write memory and for transferring said identifying information stored in said memory to said storage phosphor reader for matching said transferred information to said x-ray image signal.

BRIEF DESCRIPTION OF THE DRAWINGS

FIG. 3 is a diagrammatic view of an x-ray exam type chart shown in FIG. 1;

DESCRIPTION OF THE PREFERRED EMBODIMENT

Figure 1:
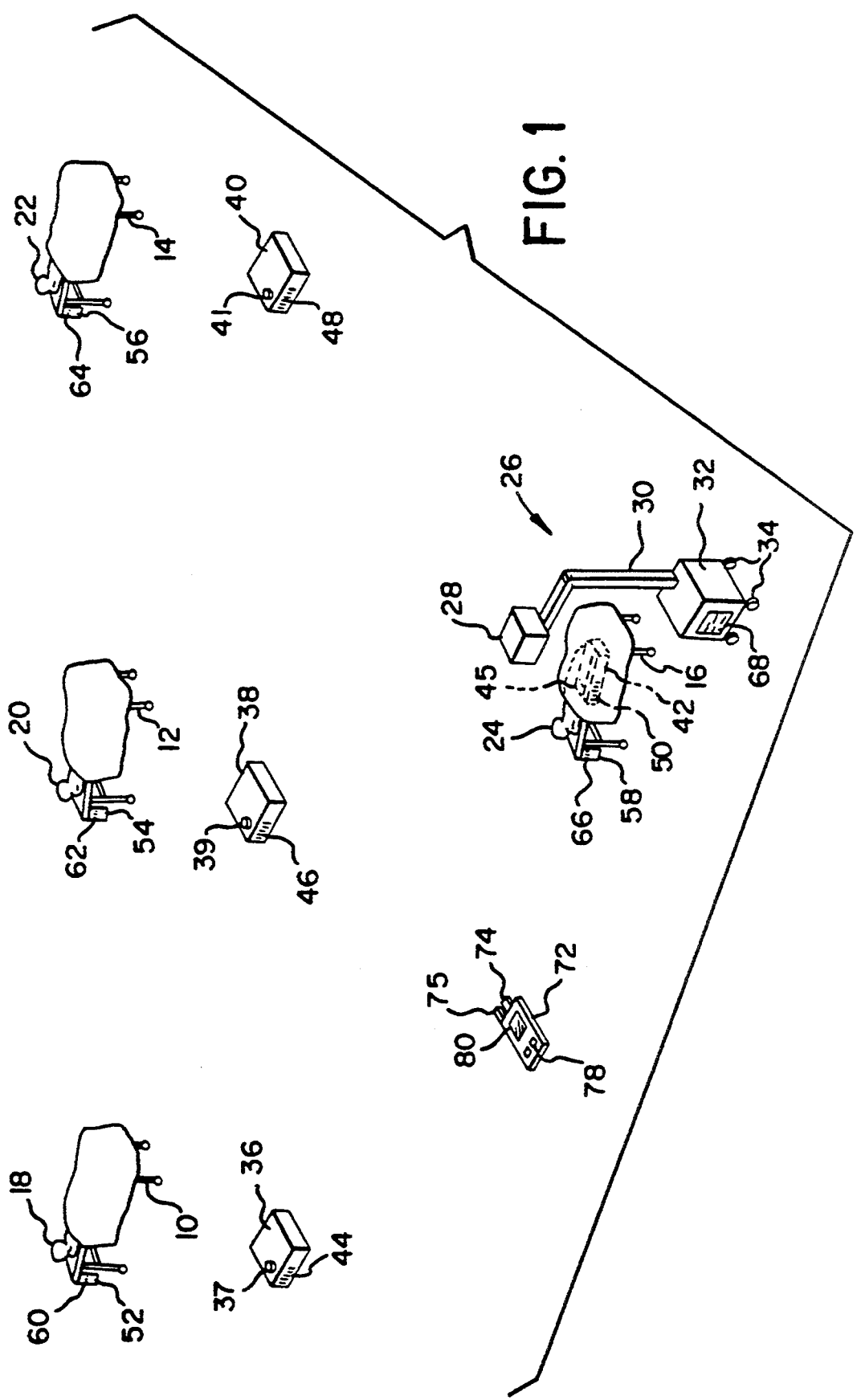
FIG. 1 is a perspective view of a medical care facility incorporating an embodiment of the present invention.

Referring now to FIG. 1, there will be described an embodiment of the present invention as used in a multibed medical care facility such as the intensive care unit of a hospital. As shown, the medical care facility includes a plurality of beds 10, 12, 14, and 16 having respective patients 18, 20, 22, and 24 who require medical treatment. A portable x-ray unit 26 has an x-ray source 28 mounted on a moveable arm 30 supported by cabinet 32. Cabinet 32 includes controls and power supply for x-ray source 28. Wheels 34 on cabinet 32 facilitate moving unit 26 from bed to bed.

According to the present invention, an x-ray image of a body part of a patient is produced in a stimulable storage phosphor contained in a cassette. Thus, storage phosphor cassettes 36, 38, 40, and 42 are provided for patients 18, 20, 22, and 24, respectively, Cassettes 36, 38, 40, and 42 have storage phosphor identifying bar codes 44, 46, 48 and 50 which uniquely identify each storage phosphor. Storage phosphor cassettes 36, 38, 40, and 42 also have adhered thereto respective read/write memories 37, 39, 41, and 45.

Figure 2:
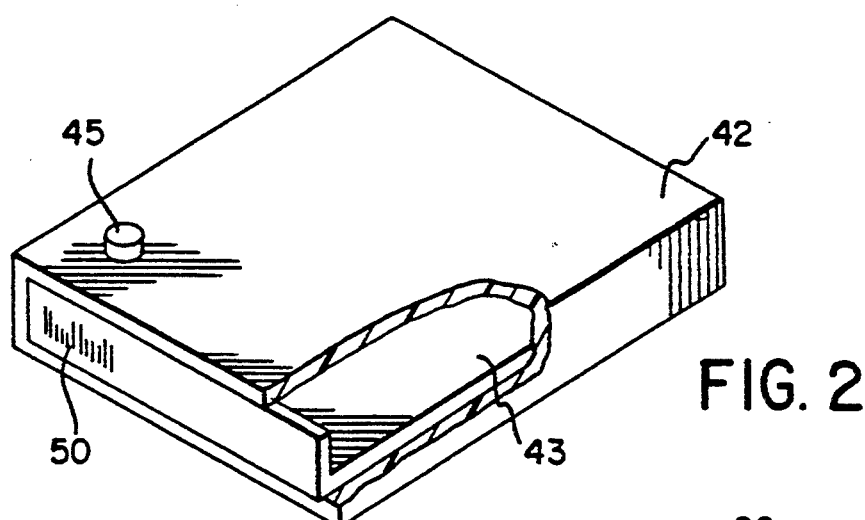
FIG. 2 is a partially broken away perspective view of a storage phosphor cassette shown in FIG. 1.
Figure 8:
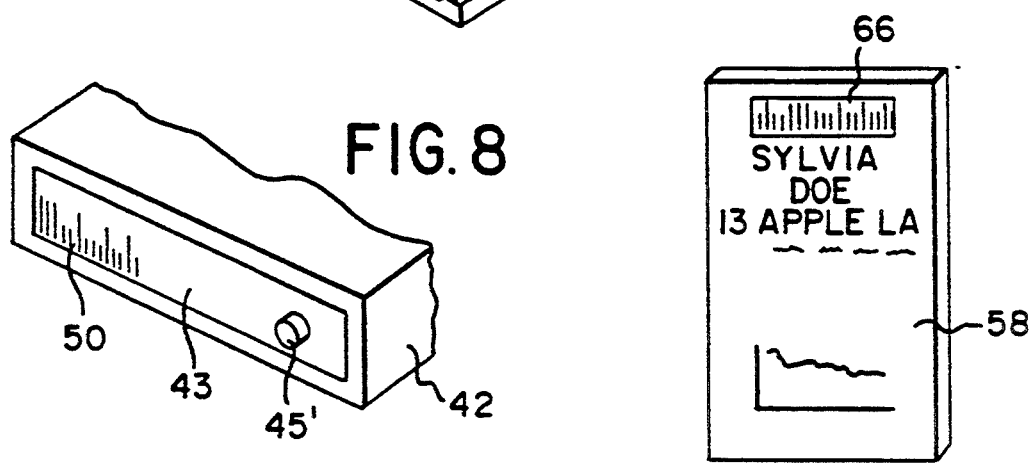
FIG. 8 is a partial perspective view of a storage phosphor cassette showing a read/write memory container adhered to a storage phosphor.
Figure 4:
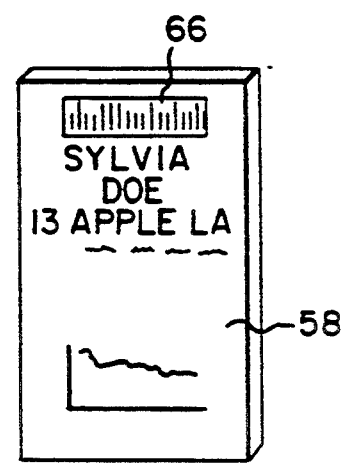
FIG. 4 is a diagrammatic view of a patient ID chart shown in FIG. 1.

As shown in FIG. 2, storage phosphor cassette 42 has a removable storage phosphor plate 43 with bar code 50. Read/write memory 45 is shown adhered to cassette 42. FIG. 8 shows an alternative placement for memory 45' as adhered to storage phosphor plate 43. An exemplary storage phosphor cassette is disclosed in commonly assigned, copending U.S. application Ser. No. 617,121.

Each patient 18, 20, 22, and 24 is provided a unique patient identifying bar code 52, 54, 56, and 58 on respective patient charts 60, 62, 64, and 66. An alternative patient identifying bar code can also be placed on an identifying bracelet placed on a patient's wrist.

X-ray unit 26 has associated with it a chart 68 having a list of x-ray exam types and/or x-ray exposure conditions with a set of bar codes identifying each exam type and exposure condition. As shown in more detail in FIG. 3, chart 68 has several sets 70A–70H of bar codes for different types of exam information. These bar code sets are illustratively described as follows. Bar code set 70A identifies x-ray source Projections, such as, AP, Lateral, RLD, LLD, X-ray Table. Bar code set 70B identifies patient Body Part, such as Chest, Skull, Abdomen, CSpine, Pelvis, Extremity. Bar code set 70C identifies patient position, such as, supine semi-erect, erect. Bar code set 70D identifies x-ray source Distance to patient, such as 40 cm, 42 cm, 45 cm, 50 cm, 72 cm. Bar code sets 70E and 70F identify x-ray source exposure parameters, respectively, kilovolts-KVP, (such as 50, 60, 70, 80, 85) and milliamperes current-MAS (such as 1.25, 1.5, 2.5, 3.2, 50, 80). Bar code set 70G identifies storage phosphor plate orientation, such as vertical, horizontal. Bar code set 70H identifies radiology technologist comments.

Figure 5:
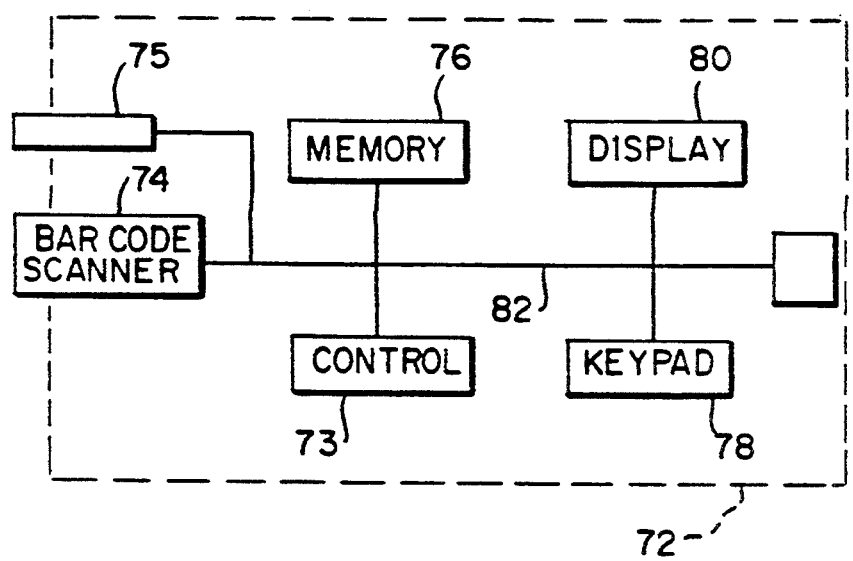
FIG. 5 is a block diagram of the bar code scanner of FIG. 1.

According to the technique of the present invention, an x-ray technician who is responsible for taking x-rays at the medical care facility is provided with a portable bar code scanner 72. Bar code scanner 72 (see FIG. 5) has a laser scanner 74 for scanning bar codes and converting the scanned bar code into an electrical signal which is stored in memory 76. Preferably, scanner 72 has a keyboard 78 for entering data which is stored in memory 76 and also has a display 80 for displaying the input data and other information. Control circuit 73, scanner 74, memory 76, display 80 and keypad 78 are internally connected by bus 82. Bar code scanner is also provided with a memory probe 75 connected to bus 82 for transferring information from scanner 72 to a memory on a storage phosphor cassette, e.g., memory 45' on cassette 42 (FIG. 8)

At the time a patient is exposed to an x-ray, a technician scans the patient identifying bar code, scans the storage phosphor identifying bar code and scans the bar code identifying the x-ray exam type. Thus, for example, as shown in FIG. 1, x-ray source 28 is positioned over patient 24 and storage phosphor cassette 42 is positioned under the chest area of patient 24. At the time of taking an x-ray, the technician uses bar code scanner 72 to scan patient identifying bar code 66 on patient chart 58, to scan storage phosphor identifying bar code 50 on storage phosphor cassette 42, and to scan x-ray examination type bar codes 70A–70H on exam type chart. A technician identifying bar code may also be read. The technician can correct or manually enter data via keypad 78 at the time an x-ray exam is effected. The technician then transfers the exam information from bar code scanner 72 to a memory 45' on the storage phosphor 43 of cassette 42.

After the technician has finished an x-ray exam of patient 24, he can move x-ray unit 26 to the bedside of patients 18, 20, and 22 to produce x-ray images in storage phosphor cassettes 36, 38, and 40.

Figure 6:
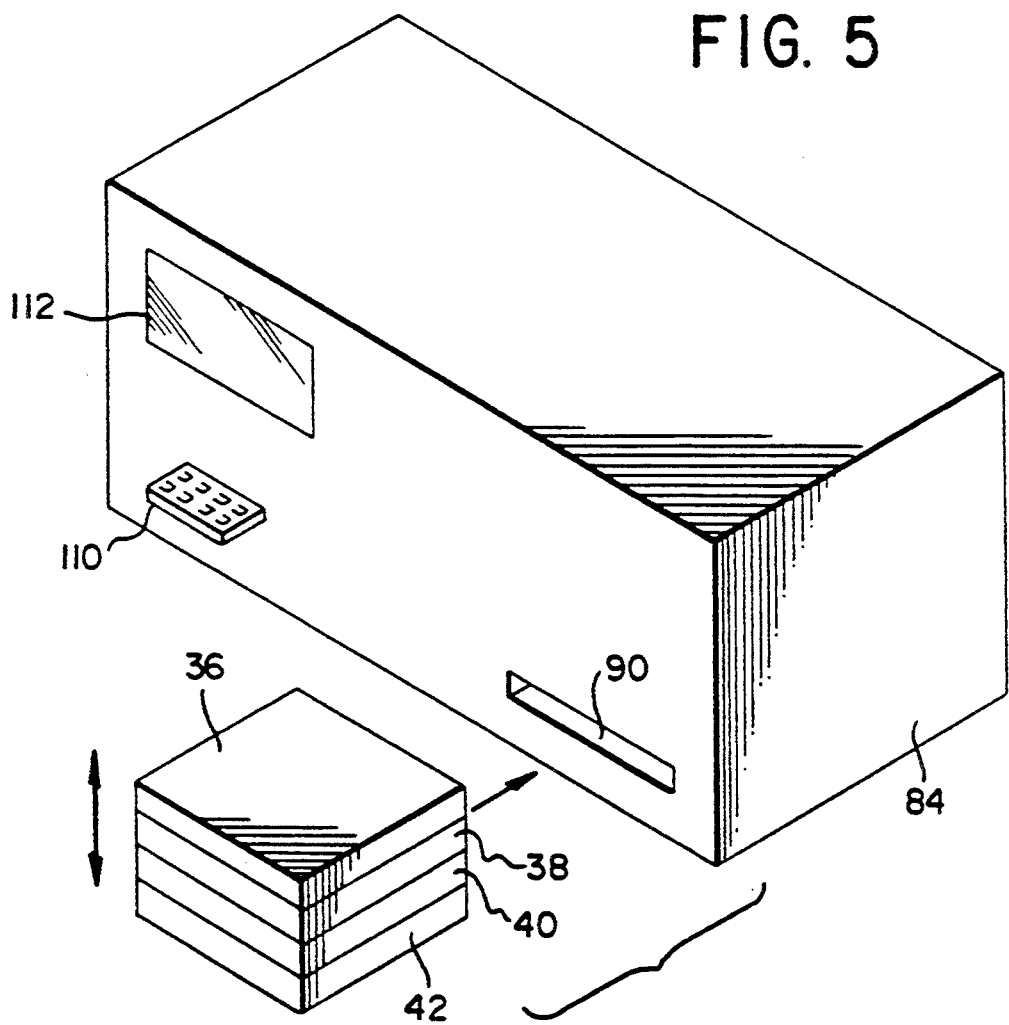
FIG. 6 is a perspective view of a storage phosphor reader for reading storage phosphors used in the system of the present invention.

After a set of x-ray exposures have been taken, relevant data for each exposure scanned by portable bar code scanner 72, and the data transferred form scanner 72 to the respective cassette memories 37, 39, 41, 45, the technician carries the storage phosphor cassettes 36, 38, 40, and 42 in a stack to a storage phosphor reader station. Such a station is shown in FIG. 6 and includes a storage phosphor reader 84 and a workstation 86. Preferably, a storage phosphor or cassette stacker (not shown) is provided adjacent to reader 84 to sequentially feed exposed storage phosphors into slot 90 of reader 84.

The exposed storage phosphor is read by reader 84 and converted to an x-ray image signal which is stored in a suitable memory. At the same time, a bar code reader in reader 84 reads the storage phosphor bar code and links the storage phosphor ID with the read x-ray image signal. As each storage phosphor is inserted into reader 84, and the stored x-ray image is converted into an x-ray image signal, the storage phosphor identifying bar code is read by a bar code reader in storage phosphor reader 84. Additionally, a memory probe in reader 84 transfers exam information from the cassette read/write memory to reader 84 where it is matched with the read x-ray image signal. Thus, the x-ray image signal read from a storage phosphor will be matched with the proper patient, x-ray exam type and other related information for further processing in workstation 86. Workstation 86 includes keyboard 110 and monitor 112.

Figure 7:
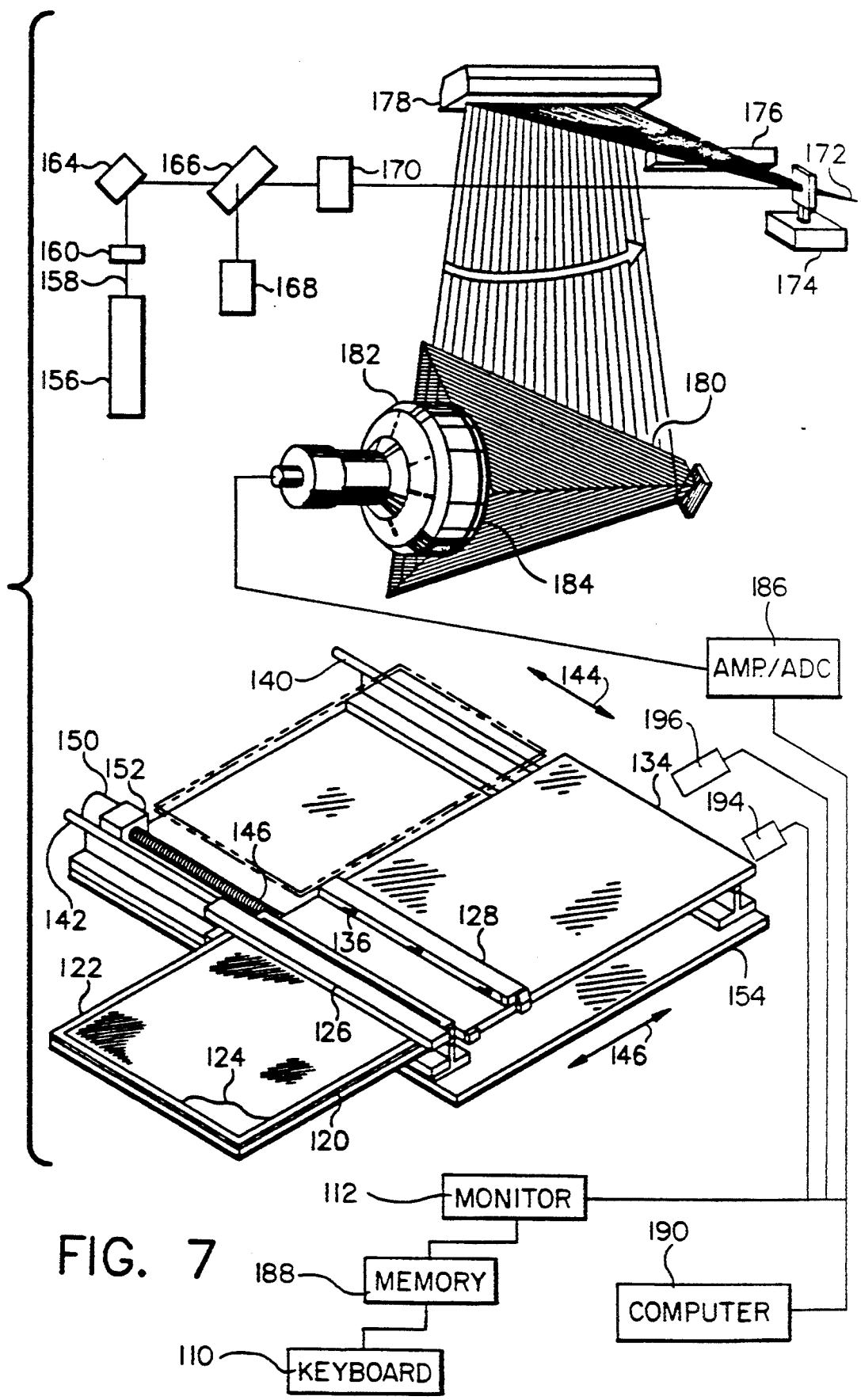
FIG. 7 is a partial block diagram, partial diagrammatic view of the storage phosphor reader shown in FIG. 6.

Referring now to FIG. 7, there is shown in more detail, storage phosphor reader 84. As shown, a storage phosphor 122 containing a storage phosphor plate 124 is loaded on cassette load platform 120. Load lever 126 is rotated to clamp cassette 122 in place and unlatches the cassette 122 by an extraction device 128. Extraction device is slidably mounted on translation stage 134 and includes hooks 136 which engage storage phosphor plate 124. Extraction device 128 extracts storage phosphor plate 124 from cassette 122 onto translation stage 134.

Translation stage 134 is slidably mounted on rails 140 and 142 for movement in opposite directions 144 which are perpendicular to the directions 146 of loading and unloading of plate 124 relative to translation stage 134. Translation stage 134 is driven by a screw motor 150 mounted on block 152. Rails 140 and 142 are supported by frame member 154 of reader 84.

The laser scanning components will now be described. Reader 84 includes a laser 156 (such as a helium neon gas laser) for stimulation of storage phosphor plate 124. Laser 156 produces a laser beam 158 which passes through a shutter 160. Beam 158 is reflected off mirror 164 and passes through beam splitter 166 which directs a portion of the laser beam 158 to reference photodetector 168. Following the beam splitter 166 laser beam 158 passes through collimator 170. The collimated laser beam is deflected by an oscillating scan mirror 172 driven by galvanometer 174. Scan mirror 172 provides the line scan raster motion of the laser beam 158. Galvanometer 174 drives mirror 172 with a constant angular velocity.

An f-theta lens 176 produces a flat field of focus and constant linear velocity at the plane of storage phosphor plate 124. Folding mirror 178 directs the laser beam through light collector 180 onto storage phosphor plate 124. Collector 180 may be of the type disclosed in commonly assigned U.S. Pat. No. 5,151,592, issued Sep. 29, 1992, inventors Boutet et al. The stimulating light of laser beam 158 causes the storage phosphor in plate 124 to emit light (blue) which is a function of the x-ray image stored in plate 124. Collector 180 directs this emitted light onto photomultiplier tube (PMT) 182. A filter 184 in front of the face of PMT 182 blocks the scattered stimulating laser light and passes the light emitted by storage phosphor plate 124. Once a storage phosphor plate 24 is on translation stage 134 a scan is begun. From the home position of stage 134, it moves under collector 180. At this point, acquisition of the latent x-ray image on storage phosphor plate 124 begins. At the end of the scan, translation stage 34 is returned to the home position.

Immediately after translation, stage 34 reaches the home position, an erase lamp (not shown) is turned on. Following a predetermined erase time (such as 30 seconds), the erase lamp is turned off and extraction mechanism 128 returns storage phosphor plate 124 in the direction of arrow 146 to storage phosphor cassette 122. The storage phosphor reader user can now rotate load lever 126 and remove cassette 122 from loading platform 120.

During the scan of storage phosphor plate 124, an emitted x-ray light image is converted by PMT 182 into an x-ray electrical current signal. This signal is converted to a digital image signal by amplifier ADC 186.

Patient identification and examination information are transferred into reader 84 from memory probe 194. As each storage phosphor plate 124 is extracted from its cassette 122 cassette bar code reader 196 reads the bar code on plate 24. The image data and corresponding patient and exam information are stored in memory 188 and correlated by computer 190.

Figure 9:
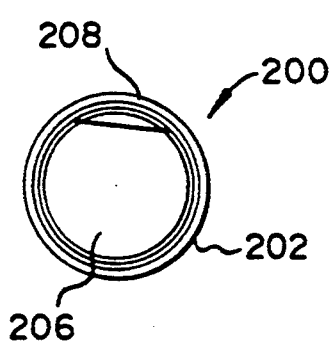
FIGS. 9 and 10 are respective top and side views of an exemplary read/write memory for incorporation in the present invention.
Figure 11:
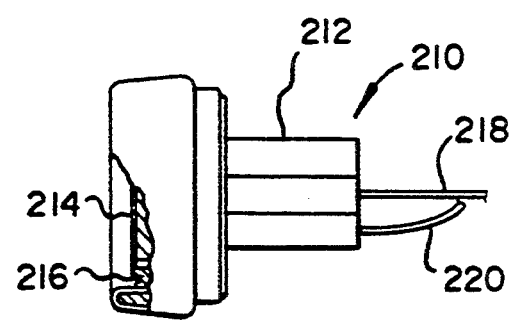
FIG. 11 is a side view of a probe for transferring information to and from the memory of FIGS. 9 and 10 and incorporated in the storage phosphor reader of FIG. 7 and in the bar code scanner shown in FIG. 5.
Figure 10:
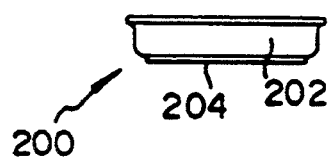

The nonvolatile read/write memory is shown in FIGS. 9 and 10. As shown, memory 200 includes a cylindrical electrically conductive (such as stainless steel) container 202 which contains a non-volatile solid state memory. Can 202 has an adhesive backing 204 which mounts memory 200 to a storage phosphor cassette or storage phosphor plate. Memory 200 has an inner face 206 which is insulated from container 202. The rim 208 of container 202 is an electrical ground contact and face 206 is a data contact. Data is transferred to and from memory 200 via the one-wire protocol which needs only a single data contact and a ground return.

FIG. 10 shows a probe 210 which is adopted to engage memory 200. Probe 210 includes a body 212 having a data contact face 214 and an electrical ground rim 216 insulated from face 214. Wires 218,220 provide connection to the system control.

Although the invention has been described with reference to preferred embodiments there, it will be understood that variations and modifications can be effected with the spirit and scope of the invention as described above as defined in the appended claims.

What is claimed is:

1. A storage phosphor cassette assembly comprising:
a storage phosphor for storing an image of an object;
a cassette for removably containing said storage phosphor:
a storage phosphor bar code located on said cassette or said storage phosphor for uniquely identifying said storage phosphor; and
a read/write non-volatile memory contained in a self-adhesive, electrically conductive container which is removably adhered to said cassette or to said storage phosphor, and which receives, stores, and transfers information relating to an image stored in said storage phosphor, relating to said storage phosphor, and/or relating to said storage phosphor cassette.

2. A hand-held bar code scanner comprising:
a scanner memory;
a light scanner for scanning a bar code and converting it to information which is stored in said memory; and
a probe connected to said scanner memory for coupling with a read/write non-volatile memory contained in a container removably adhered with a storage phosphor/cassette to transfer information between said scanner memory and said read/write non-volatile memory.

3. The hand-held bar code scanner of claim 2 including a keypad for entering instructions and data into said scanner and a display for displaying data and information.

4. A storage phosphor identification system comprising:
a storage phosphor cassette assembly including a storage phosphor for storing an image of an object, a cassette for removably containing said storage phosphor, and a storage phosphor bar code located on said cassette or said storage phosphor for uniquely identifying said storage phosphor;
a read/write non-volatile memory contained in a self-adhesive, electrically conductive container which is removably adhered to said cassette or to said storage phosphor, and which receives, stores, and transfers information;
a hand-held bar code scanner having a probe for coupling with said read/write non-volatile memory and for transferring information to be stored therein; and
a storage phosphor reader for converting a stored image in said storage phosphor into an image signal, said storage phosphor reader having, a) a bar code reader for reading said storage phosphor bar code to produce a storage phosphor identifying signal matched with said image signal; and b) a read/write memory probe for coupling with said read/write memory and for transferring information stored in said memory to said storage phosphor reader for matching said transferred information with said image signal.

5. A storage phosphor cassette assembly comprising:
a storage phosphor for storing an image of an object;
a cassette for removably containing said storage phosphor:
a storage phosphor bar code located on said cassette or said storage phosphor for uniquely identifying said storage phosphor; and
a read/write non-volatile memory including a self-adhesive, electrically conductive container which is removably adhered to said cassette or to said storage phosphor and further including an inner face which is insulated from said container, and which receives, stores, and transfers information relating to an image stored in said storage phosphor, relating to said storage phosphor, and/or relating to said storage phosphor cassette through a data contact with said inner face and a ground return contact with said container.

* * * * *